(12) United States Patent
Lavielle et al.

(10) Patent No.: US 7,026,357 B2
(45) Date of Patent: Apr. 11, 2006

(54) DIPHENYLUREA COMPOUNDS

(75) Inventors: Gilbert Lavielle, La Celle Saint Cloud (FR); Olivier Muller, Ennery (FR); Mark Millan, Le Pecq (FR); Anne Dekeyne, Saint Remy les Chevreuses (FR); Mauricette Brocco, Paris (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/862,546

(22) Filed: Jun. 7, 2004

(65) Prior Publication Data

US 2004/0224993 A1 Nov. 11, 2004

Related U.S. Application Data

(62) Division of application No. 09/896,278, filed on Jun. 29, 2001, now Pat. No. 6,784,183.

(30) Foreign Application Priority Data

Jun. 29, 2000 (FR) .................................. 00 08378

(51) Int. Cl.
*A61K 31/17* (2006.01)
*C07D 233/02* (2006.01)
*C07D 401/00* (2006.01)
*C07D 211/70* (2006.01)
*C07C 273/00* (2006.01)

(52) U.S. Cl. ...................... 514/596; 514/597; 514/422; 548/311.4; 548/341.5; 548/342.5; 546/336; 564/50; 544/362

(58) Field of Classification Search ............. 548/311.1, 548/336.1, 342.5, 341.5, 311.4; 514/422, 514/357, 596, 597; 564/50; 544/362
See application file for complete search history.

(56) References Cited

OTHER PUBLICATIONS

Robert Aslanian et al., Identification of a Novel, Orally Bioavailable Histamine H3 Receptor Antagonist Based on the 4-Benzyl-(1H-imidazol-4-yl)Template, Bioorganic & Medicinal Chemistry Letters 12(2002) 937-941.*
Christine-Brefel-Courbon et al., alpha-2 Adrenoceptor Antagonists, A New Approach to Parkinson's Disease, Drug Therapy, CNS Drugs 1998 Sep.: 10(3).*
Gaster et al., Latest Developments in Serotonin Receptor Modulation, Annual Reports in Medicinal Chemistry.*
Clark, et al., *Neuroendocrinology*, 41: 36-43 (1985).
Reid, et al., *Lancet* pp. 421-423 Aug. 22, (1987).
Smith, et al., *Physiology & Behavior*, 41: 7-14 (1987).
Bitran, et al., *Neuroscience & Biobehavioral Reviews*, 11: 365-389 (1987).
Danjou, et al., *B J Clin Pharmac*, 26: 733-739 (1988).
Susset, et al., *J Urology*, 141: 1360-1363 (1989).
Riley et al., *Sexual and Marital Therapy*, 4:17-26 (1989).
Koskinen, et al., *Physiology & Behavior*, 50: 589-593 (1991).
Jacobsen, et al., *J. Clin Psychiatry*, 53:119-122 (1992).
Montorsi, et al., *Urology*, 44(5): 732-736 (1994).
Carey, et al., *Archives of Sexual Behavior*, 25(4): 341-360 (1996).
Vogt, et al., *Intl J Impotence Res*, 9: 155-161 (1997).
Kunelius, et al., *Urology*, 49(3): 441-444 (1997).
Morales, et al., *Intl J Impotence Res*, 12(S1): S70-S74 (2000).
Goldstein, et al., *Intl J Impotence Res*, 12(S1): S75-S80 (2000).
Goldstein, et al., *World J Urology*, 19: 51-56 (2001).
Foreman, et al., *Life Sciences*, 45(14): 1263-1270 (1989).
Watson, et al., *Pharmacology Biochemistry & Behavior*, 39: 605-612 (1991).
Klint, et al., *Psychopharmacology*, 119: 291-294 (1995).
Popova, et al., *Neuroendocrinology* 76: 28-34 (2002).

(Continued)

*Primary Examiner*—Johann Richter
*Assistant Examiner*—Ebenezer Sackey
(74) *Attorney, Agent, or Firm*—Hueschen and Sage

(57) ABSTRACT

Compound of formula (I):

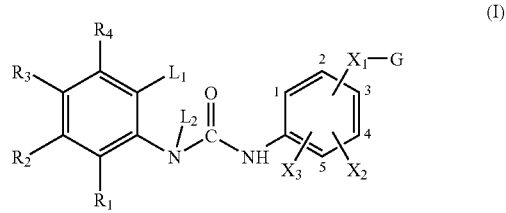

and medicinal products containing the same are useful as dual $\alpha_2/5\text{-HT}_{2c}$ antagonist receptors.

15 Claims, No Drawings

OTHER PUBLICATIONS

O'Neill, et al., *Pharmacology Biochemistry & Behavior*, 63(2): 237-243 (1999).
Kettle, et al., *British J Pharmacology*, 126: 572-574 (1999).
Herrick-Davis, et al., *J Pharmacology & Exp Therapeutics*, 295(1):226-232 (2000).
Wood, et al., *Drug Dev Res*, 54: 88-94 (2001).
Sodhi, et al., *Molecular Psychiatry*, 6: 373-379 (2001).
Abi-Saab, et al., *Psychopharmacology*, 162: 55-62 (2002).
Hertel, et al., *Science*, 286: 105-107 (1999).
Litman, et al., *British J Psychiatry*, 168:571-579 (1996).
Sara, et al., *Behavioral and Neural Biology*, 51: 401-411 (1989).
Smith, et al., *J Psychopharmacology*, 6(3):376-381 (1992).
Coull, et al., *Psychopharmacology*, 123: 239-249 (1996).
Pascual, et al., *Neuroscience Letters*, 142: 36-40 (1992).
Tellez, et al., *Eur J Pharmacology*, 277: 113-116 (1995).
Sirvio, et al., *Pharmacology Biochem & Behavior*, 45: 123-129 (1993).
Haapalinna, et al., *Eur J Pharmacology*, 347: 29-40 (1998).
Chopin, et al., *J Pharmacology & Exp Therapeutics*, 301(1): 187-196.
Paiva, et al., *Psychopharmacology*, 96:395-399 (1988).
Landolt, et al., *Neuropsychopharmacology*, 21:455-466 (1999).
Sharpley, et al., *Biological Psychiatry*, 47:468-470 (2000).
Smith, et al., *Pharmacological Biochemistry and Behavior*, 71:599-605 (2002).
Advanced Organic Chemistry, IV Ed, John Wiley & Sons, New York (1992).
Berendsen, et al., *Psychopharmacology*, 101, 56-61 (1990).
Millan, et al., *Eur. J. Pharmacol*, 325, 9-12 (1997).
Millan, et al., *J. Pharmacol. Exp. Ther.*, 298 (2), 581-591 (2001).
Shih, et al., *Brain Research*, 835, 104-112 (1999).
Koskinen, et al., *Pharmacol. Biochem. Behav.*, 66(4), 729-738 (2000).
Fox, et al., *Drug News Perspect.*, 12(8), 477-483 (1999).
Smith, et al., *J. Psychopharmacol.*, 6(3), 376-381 (1992).
Millan, et al., *Eur. J. Neurosci*, 12, 1079-95 (2000).
DeBoer, et al., *J. Pharmacol. Exp. Ther.*, 277(2), 852-60 (1997).
Haddjeri, et al., *Naunyn-Schmiedeberg's Archiv. Pharmacol.*, 355(1), 20-9 (1997).
Nutt, *J. Psychopharmacol.*, 8(4), 193-195 (1994).
Lindstrom, *Trends Pharmacol. Sci.*, 21(6), 198-199 (2000).
Millan, et al., *J. Pharmacol. Exp. Ther.*, 292(1), 54-66 (2000).
Cussac, et al., *Nauyn-Schmiedeberg's Arch. Pharmacol.*, 361(2), 549-54 (2000).
Reavill, et al., *Br. J. Pharmacol.*, 126(3), 572-574 (1999).
Gobert, et al., *Synapse*, 36(3), 205-221 (2000).
Lane, *J. Pyschopharmacol.*, 11(1), 72-82 (1997).
O'Neill, et al., *Pharmacology, Biochemistry and Behavior*, 1999, 63, 237-243.
Reavill, et al., *British Journal of Psychopharmacology*, 1999, 126, 572-574.
Herrick-Davis, et al., *Journal of Pharmacology and Experimental Therapeutics*, 2000, 295, 226-232.
Wood, et al., *Drug Development Research*, 2001, 54, 88-94.
Paiva, et al., *Psychopharmacology*, 1988, 96, 395-399.
Dugovic, *Journal Sleep Research*, 1992, 1, 1163-1168.
Landolt, et al., *Neuropsychopharmacology*, 1999, 21, 455-466.
Sharpley, et al., *Biological Psychiatry*, 2000, 47, 468-470.
Foreman, et al., *Life Sciences*, 1989, 45, 1263-1270.
Klint, et al., *Psychopharmacology*, 1995, 119, 291-294.
Hirschfeld, *Journal of Clinical Psychiatry*, 60 Suppl. 17:32-35, 1999.
Popova, et al., *Neuroendocrinology*, 2002, 76, 28-34.
McMahon, et al., *Journal of Neuroscience*, 2001, 21, 7781-7787.
Filip, et al., *Pharmacology, Biochemistry and Behaviour*, 2002, 71, 545-756.
Fox, et al., *Drug News and Perspectives*, 1999, 12:477-483.
Fox, et al., *Movement Disorders*, 2000, 15:1064-1069.
Berendsen, et al., *Psychopharmacology*, 1990, 101, 57-61.
Millan, et al., *European Journal of Pharmacology*, 1997, 325, 9-12.
Koskinin, et al., *Pharmacology, Biochemistry and Behaviour*, 2000, 66, 729-738.
White, et al., *Pharmacology, Biochemistry and Behaviour*, 1991, 39, 729-736.
Millan, et al., *Journal of Pharmacology and Experimental Therapeutics*, 2001, 298, 581-591.
Mundo, et al., *International Clinical Psychopharmacology*, 2000, 15, 69-76.
Sara, et al., *Behavioural Neural Biology*, 1989, 51, 401-411.
Smith, et al., *Journal of Psychopharmacology*, 1992, 6, 376-381.
Coull, et al., *Psychopharmacology*, 1996, 123, 239-249.
Telles, et al., *European Journal of Pharmacology*, 1995, 277, 113-116.
Haapalinna, et al., *European Journal of Pharmacology*, 1998, 347, 29-40.
"Dexefaroxan, efaroxan, L-0046, RX-821037", *Pharmaproject*, Phase II Clinical Trial (2005).
Nutt, *J. Psychopharmacology*, 1994, 8, 193-195.
Litman, et al., *British Journal of Psychiatry*, 1996, 168, 571-579.
Hertel, et al., *Science*, 1999, 286, 105-107.
"Idazoxan, CGP-25811A, LO022, RX-781094", *Pharmaproject*, Phase II Clinical Trial (2005).
"Fipamezol, JP-1730", *Pharmaproject*, Phase II Clinical Trial (2005).
Grondin, et al., *Naunyn Schmiedebergs Archives of Pharmacology*, 2000, Feb:361, 181-186.
Rascol, et al., *Mov. Disord.*, 2001, 16, 708-713.
Brown, et al., *Investigational Drugs*, 2002, 5, 454-468.
Clark, et al., *Neuroendocrinology*, 1985, 41, 36-43.
Reid, et al., *Lancet*, 1987, 22, (8556):421-423.
Koskinen, et al., *Physiology and Behaviour*, 1991, 50, 589-593.
Kunelius, et al., *Urology*, 1997, 49, 441-444.

* cited by examiner

DIPHENYLUREA COMPOUNDS

The present invention relates to new diphenylurea compounds.

The invention relates also to their use as mixed $\alpha_2$/5-HT$_{2c}$ ligands.

DESCRIPTION OF THE PRIOR ART

Compounds having a diphenylurea structure have been described in the Application JP 11130750 for their serotonergic antagonistic properties, and in the Application WO 99 32436 for their use as raf kinase inhibitors.

BACKGROUND OF THE INVENTION

The frontal cortex plays an essential role in the processes that control the functions affected in psychiatric disorders. In particular, it is now accepted that the disturbance of monoaminergic transmission is strongly implicated in the etiology of those various disorders. For example, in the case of depression, monoaminergic activity is reduced in the corticolimbic regions.

Among the various monoamine auto- and hetero-receptors implicated in regulatory mechanisms, $\alpha_2$-A.R. (autoreceptors) and 5-HT$_{2c}$ receptors have proved to be of major importance. Those two receptor sub-types act in the same way by inhibiting dopaminergic and adrenergic transmission. On the one hand a retrocontrol is exerted by $\alpha_2$-A.R. receptors on noradrenergic neurons (J. Pharmacol. Exp. Ther., 1994, 270, 958), and on the other hand 5-HT$_{2c}$ receptors exert an inhibiting control on dopaminergic and noradrenergic transmission (Neuropharmacology, 1997, 36, 609).

In the past, compounds binding one or the other of those receptor sub-types have demonstrated their potential in the treatment of a plurality of pathologies.

For example, the beneficial role of $\alpha_2$ antagonist compounds has been studied in the treatment of cognitive disorders (J. Pharmacol., 1992, 6, 376), Parkinson's disease (CNS Drugs, 1998, 10, 189), libido disorders and sexual dysfunction (J. Pharmacol., 1997, 11, 72). Similarly, 5HT$_{2c}$ receptor antagonist compounds have demonstrated their usefulness in the treatment of sexual dysfunction (ref. J. Pharmacol., ibid.), Parkinson's disease (Drug News Perspect., 1999, 12, 477), and also anxiety (Br. J. Pharmacol., 1996, 117, 427) and schizophrenia (Neurosci. Lett., 1996, 181, 65).

Compounds having a dual $\alpha_2$-A.R. and 5-HT$_{2c}$ antagonist character may be of significant use for clinicians for achieving, with the administration of a single compound, an appreciably enhanced action in the restoration of neurotransmission by means of a synergistic effect. That kind of compound furthermore presents a considerable advantage in comparison with the administration of two different products.

The compounds of the invention have a novel structure that confers on them such a dual $\alpha_2$/5-HT$_{2c}$ antagonist character, and they are accordingly useful in the treatment of depression, anxiety, schizophrenia, Parkinson's disease, cognitive disorders, libido disorders and sexual dysfunction, sleep disorders, drug abuse, and impulsive behaviour disorders.

DETAILED DESCRIPTION OF THE INVENTION

The present invention relates to the compounds of formula (I):

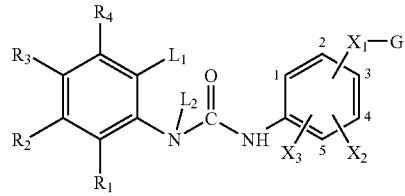

wherein:
R$_1$, R$_2$, R$_3$ and R$_4$ independently represent a hydrogen atom, a halogen atom or an alkyl, alkoxy, hydroxy, alkylthio, mercapto, cyano, amino (optionally substituted by one or two alkyl groups), nitro, carboxy, alkoxycarbonyl, aminocarbonyl (optionally substituted by one or two alkyl groups) or carbamoyl group, or, taken in pairs, form together with the carbon atoms to which they are bonded a phenyl ring or an aromatic heterocycle having from 5 to 7 ring members and containing from 1 to 3 hetero atoms selected from nitrogen, oxygen and sulphur, L$_1$ and L$_2$ each represents a hydrogen atom or together form a —CH$_2$—CH$_2$— group, X$_1$, attached at the 2 or 3 position of the aromatic ring, represents a bond, and in that case X$_2$ represents a hydrogen atom, a halogen atom, an alkyl, alkoxy, hydroxy, nitro or cyano group, or an amino group (optionally substituted by one or two alkyl groups), or, X$_1$ and X$_2$, together with two adjacent carbon atoms to which they are bonded in the 2, 3 or 4 position of the aromatic ring, form a (C$_4$–C$_7$)cycloalkyl group wherein one or two —CH$_2$— groups of the cycloalkyl ring are optionally replaced by an oxygen atom or an NH group (optionally substituted by an alkyl group), and wherein one carbon atom of the cycloalkyl ring is substituted by the group G, X$_3$ represents a hydrogen atom, a halogen atom, an alkyl, alkoxy, hydroxy, nitro or cyano group, or an amino group (optionally substituted by one or two alkyl groups), G represents a group selected from:

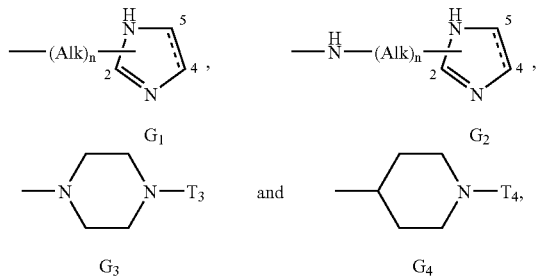

wherein:
the broken lines indicate the optional presence of a double bond,

Alk represents a linear or branched $(C_1-C_6)$alkylene group wherein, when $G_1$ or $G_2$ contains an imidazoline group, the group Alk- is attached at the 2 position of the ring, n is 0 or 1, $T_3$ represents an alkyl, optionally substituted aryl, optionally substituted arylalkyl, optionally substituted heteroaryl or optionally substituted heteroarylalkyl group, $T_4$ represents an alkyl, optionally substituted aryl, optionally substituted arylalkyl, optionally substituted heteroaryl or optionally substituted heteroarylalkyl group, wherein:

the term "alkyl" denotes a linear or branched group containing from 1 to 6 carbon atoms, the term "alkoxy" denotes a linear or branched alkyl-oxy group containing from 1 to 6 carbon atoms, the term "aryl" denotes a phenyl, naphthyl or biphenyl group, the term "heteroaryl" denotes an aromatic monocyclic group, or a bicyclic group in which at least one of the rings is aromatic, each group containing from 5 to 11 ring members and from 1 to 5 hetero atoms selected from nitrogen, oxygen and sulphur, the expression "optionally substituted" associated with the groups aryl, arylalkyl, heteroaryl and heteroarylalkyl denotes that those groups are unsubstituted or substituted on the cyclic moiety by one or more halogen atoms and/or alkyl, alkoxy, hydroxy, mercapto, alkylthio, cyano, amino (optionally substituted by one or two alkyl groups), nitro, carboxy, alkoxycarbonyl, aminocarbonyl (optionally substituted by one or two alkyl groups) or carbamoyl groups, wherein the heteroaryl and heteroarylalkyl groups may in addition be substituted by an oxo group, to enantiomers and diastereoisomers thereof, and also to addition salts thereof with a pharmaceutically acceptable acid or base.

Among the pharmaceutically acceptable acids there may be mentioned hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned sodium hydroxide, potassium hydroxide, triethylamine, tert-butylamine, etc.

In preferred compounds of formula (I), $R_1$ and $R_4$ each represents a hydrogen atom.

In compounds of formula (I), $R_2$ and $R_3$ are advantageously selected from a halogen atom and an alkyl group.

An advantageous embodiment of the invention relates to compounds of formula (I) wherein $X_1$ is attached at the 2 position of the phenyl ring.

Another advantageous embodiment of the invention relates to compounds of formula (I) wherein, when $L_1$ and $L_2$ together form a —$CH_2$—$CH_2$— group, $R_3$ and $R_4$, together with the carbon atoms to which they are bonded, form a phenyl ring.

Preferred compounds of the invention are those wherein $X_1$ represents a bond and $X_2$ represents a halogen atom or an alkyl or alkoxy group.

Another advantageous embodiment of the invention relates to compounds of formula (I) wherein $X_3$ represents a hydrogen atom.

In preferred compounds of formula (I), G will advantageously be selected from the groups $G'_1$, $G''_1$, $G'_2$ and $G'_3$ wherein T'3 will be more especially an optionally substituted heteroaryl group or optionally substituted heteroarylalkyl group.

Other preferred compounds of the invention are those wherein $X_1$ and $X_2$, together with the two carbons in the 2 and 3 positions of the aromatic ring to which they are bonded, form a $(C_4-C_7)$cycloalkyl group, for example a cyclopentyl group.

The aryl group preferred according to the invention is the phenyl group.

Among the preferred compounds of the invention, the following, more especially, may be mentioned:

N-(3-chloro-4-methylphenyl)-N'-{3-[4-(2,3-dihydro-1,4-benzodioxin-2-ylmethyl)-1-piperazinyl]phenyl}urea, N-[4-chloro-3-(4,5-dihydro-1H-imidazol-2-ylamino)phenyl]-N'-(3-chloro-4-methylphenyl)urea, N-(3-chloro-4-methylphenyl)-N'-[2-(1H-imidazol-4-yl)-indan-5-yl]urea, N-{3-[4-(2,3-dihydro-1,4-benzodioxin-2-ylmethyl)-1-piperazinyl]phenyl}-N'-(3, 4-dimethylphenyl)urea, The invention extends also to a process for the preparation of the compounds of formula (I).

One process for the preparation of the compounds of formula (I) is characterised in that there is used as starting material an aromatic amine of formula (II)

(II)

wherein $X_1$, $X_2$, $X_3$ and G are as defined for formula (I), which is condensed by heating in basic medium with a compound of formula (III):

(III)

wherein $R_1$, $R_2$, $R_3$ and $R_4$ are as defined for formula (I), to yield the compound of formula (I/a):

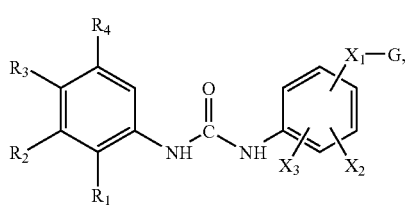

(I/a)

a particular case of the compounds of formula (I) wherein $R_1$, $R_2$, $R_3$, $R_4$, $X_1$, $X_2$, $X_3$ and G are as defined hereinbefore, wherein the isocyanate of formula (III) is either commercially available or is prepared according to known procedures, for example from the corresponding carboxylic acid by reaction with sodium azide and rearrangement of the acyl azide obtained, which compounds of formula (I/a)
- may, if necessary, be purified according to a conventional purification technique,
- are optionally separated into isomers according to a conventional separation technique,
- are, if desired, converted into addition salts with a pharmaceutically acceptable acid or base.

Another process for the preparation of the compounds of formula (I) is characterised in that there is used as starting material an amine of formula (IV):

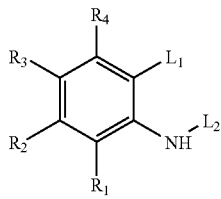

(IV)

wherein $L_1$, $L_2$, $R_1$, $R_2$, $R_3$ and $R_4$ are as defined for formula (I), which is condensed by heating in basic medium with a compound of formula (V):

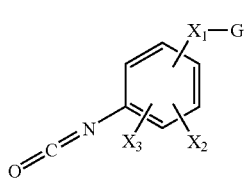

(V)

wherein $X_1$, $X_2$, $X_3$ and G are as defined for formula (I), to yield the compound of formula (I/b):

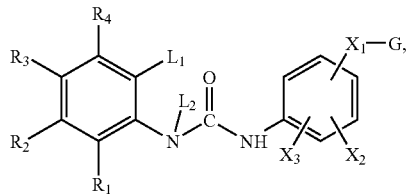

(I/b)

a particular case of the compounds of formula (I) wherein $R_1$, $R_2$, $R_3$, $R_4$, $L_1$, $L_2$, $X_1$, $X_2$, $X_3$ and G are as defined hereinbefore, wherein the isocyanate of formula (V) is either commercially available or is prepared according to known procedures, for example from the corresponding carboxylic acid by reaction with sodium azide and rearrangement of the acyl azide obtained, which compounds of formula (I/b)
- may, if necessary, be purified according to a conventional purification technique,
- are optionally separated into isomers according to a conventional separation technique,
- are, if desired, converted into addition salts with a pharmaceutically acceptable acid or base.

Another process for the preparation of the compounds of formula (I) is characterised in that there is used as starting material an amine of formula (VI):

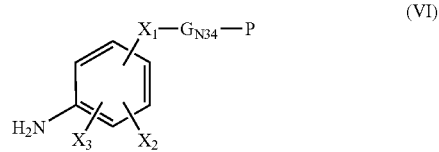

(VI)

wherein $X_1$, $X_2$ and $X_3$ are as defined for formula (I), $G_{N34}$ represents an NH group or a 1-piperazinyl or 4-piperidinyl group, and P represents a hydrogen atom or a group protecting the amine function, which is condensed by heating in basic medium with a compound of formula (III):

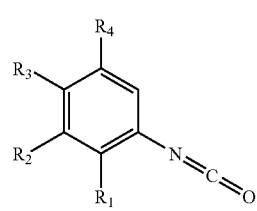

(III)

wherein $R_1$, $R_2$, $R_3$ and $R_4$ are as defined for formula (I), to yield the compound of formula (VII):

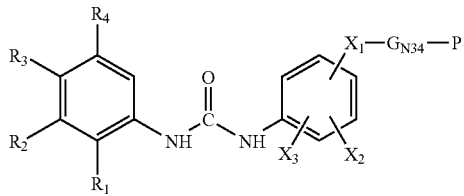

(VII)

wherein $R_1$, $R_2$, $R_3$, $R_4$, $X_1$, $X_2$, $X_3$, $G_{N34}$ and P are as defined hereinbefore, which compound of formula (VII), when $G_{N34}$ represents a 1-piperazinyl or 4-piperidinyl group, after deprotection where necessary of the amine function, is subjected to a substitution reaction in basic medium to yield the compound of formula (I/c):

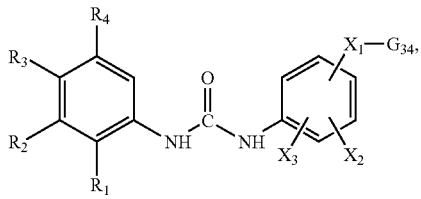

(I/c)

a particular case of the compounds of formula (I) wherein $R_1$, $R_2$, $R_3$, $R_4$, $X_1$, $X_2$ and $X_3$ are as defined hereinbefore and $G_{34}$ represents a group $G_3$ or $G_4$ as defined for formula (I), or when $G_{N34}$ represents an NH group, after deprotection where necessary, is condensed with thiophosgene to yield the compound of formula (VIII):

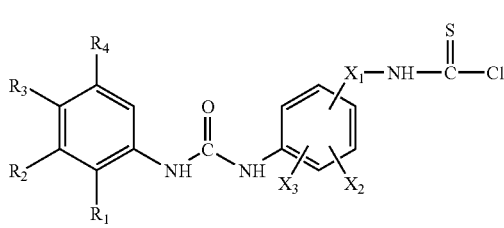

(VIII)

wherein $R_1$, $R_2$, $R_3$, $R_4$, $X_1$, $X_2$ and $X_3$ are as defined hereinbefore, which is subjected to the action of ethylenediamine to yield the compound of formula (IX):

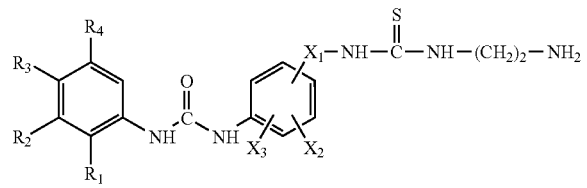

(IX)

wherein $R_1$, $R_2$, $R_3$, $R_4$, $X_1$, $X_2$ and $X_3$ are as defined hereinbefore, which compound of formula (IX) is subjected to an intramolecular cyclisation reaction catalysed by a palladium compound to yield the compound of formula (I/d):

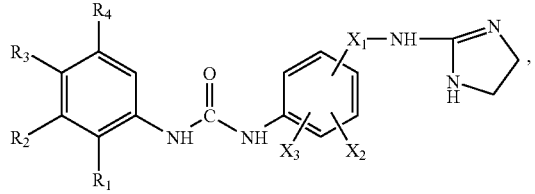

(I/d)

a particular case of the compounds of formula (I) wherein $R_1$, $R_2$, $R_3$, $R_4$, $X_1$, $X_2$ and $X_3$ are as defined hereinbefore, which compounds of formulae (I/c) and (I/d), may, if necessary, be purified according to a conventional purification technique, are optionally separated into isomers according to a conventional separation technique, are converted, if desired, into addition salts with a pharmaceutically acceptable acid or base.

The present invention relates also to pharmaceutical compositions comprising as active ingredient at least one compound of formula (I), alone or in combination with one or more pharmaceutically acceptable, inert, non-toxic excipients or carriers.

Among the pharmaceutical compositions according to the invention there may be mentioned more especially those which are suitable for oral, parenteral, nasal or transdermal administration, tablets or dragees, sublingual tablets, gelatine capsules, lozenges, suppositories, creams, ointments, dermal gels etc.

The useful dosage varies according to the age and weight of the patient, the nature and severity of the disorder and the administration route, which may be oral, nasal, rectal or parenteral. Generally, the unit dosage ranges from 0.05 mg to 500 mg for a treatment of from 1 to 3 administrations per 24 hours.

The following Examples illustrate the invention and do not limit it in any way. The structures of the compounds described were confirmed by customary spectroscopic techniques.

The starting materials used are known products or are prepared according to known procedures.

Preparation A: 3-(4,5-Dihydro-1H-imidazol-2-ylmethyl) aniline

Step 1: 2-(3-Nitrobenzyl)-4,5-dihydro-1H-imidazole hydrochloride

A mixture of 30.7 mmol (5 g) of 3-nitrophenylacetonitrile and 30 mmol (7.2 g) of ethylenediamine para-toluenesulphonate is heated at 100° C. for 1 hour. After cooling to 20° C., the mixture is hydrolysed with 100 ml of a 5M aqueous solution of sodium hydroxide and then extracted with dichloromethane. The organic phases are dried over magnesium sulphate and concentrated. The residue obtained is converted into the hydrochloride by the action of an ethanolic HCl solution to yield the expected product.

Step 2: 3-(4,5-Dihydro-1H-imidazol-2-ylmethyl)aniline

A solution of 22.7 mmol (5.5 g) of the product described in the above Step in a mixture of 100 ml of ethanol and 10 ml of water is stirred under a hydrogen atmosphere in the presence of 0.5 g of 10% palladium-on-carbon. When the absorption of hydrogen has ceased, the reaction mixture is filtered and concentrated to yield the expected product.

Preparation B: 3-[1-(4,5-Dihydro-1H-imidazol-2-yl)ethyl] aniline

Step 1: 2-(3-Nitrophenyl)propanenitrile

A mixture of 62 mmol (10 g) of 3-nitrophenylacetonitrile, 1.11 mol (100 g) of dimethyl carbonate and 3.1 mmol (0.43 g) of potassium carbonate is heated for 6 hours at 170° C. in an autoclave. After cooling, 200 ml of dichloromethane are added and the organic phase is washed with 100 ml of water and then with 100 ml of a saturated aqueous solution of sodium chloride. The organic phase is dried over magnesium sulphate and concentrated. The residue obtained is purified by chromatography on silica gel, using as eluant a 90/10 cyclohexane/ethyl acetate mixture, to yield the expected product.

Step 2: 2-[1-(3-Nitrophenyl)ethyl]-4,5-dihydro-1H-imidazole

The expected product is obtained in accordance with the procedure described in Preparation A, Step 1, using as starting material the compound described in the above Step.

Step 3: 3-[1-(4,5-Dihydro-1H-imidazol-2-yl)ethyl]aniline

The expected product is obtained in accordance with the procedure described in Preparation A, Step 2, using as starting material the compound described in the above Step.

Preparation C: 3-[1-(4,5-Dihydro-1H-imidazol-2-yl)-1-methylethyl]aniline

Step 1: 2-Methyl-2-(3-nitrophenyl)propanenitrile 40 ml of 50% sodium hydroxide solution are added to a vigorously stirred solution of 123 mmol (20 g) of 3-nitrophenylacetonitrile and 369 mmol (46.5 g) of dimethyl sulphate in 200 ml of dimethyl sulphoxide. After stirring for one hour, the reaction mixture is diluted with 2 litres of water and extracted twice with 1 litre of diethyl ether. The organic phases are dried over sodium sulphate and concentrated to yield the expected product.

Step 2: 2-[1-Methyl-1-(3-nitrophenyl)ethyl]-4,5-dihydro-1H-imidazole

The expected product is obtained in accordance with the procedure described in Preparation A, Step 1, using as starting material the compound described in the above Step.

Step 3: 3-[1-(4,5-Dihydro-1H-imidazol-2-yl)-1-methylethyl]aniline

The expected product is obtained in accordance with the procedure described in Preparation A, Step 2, using as starting material the compound described in the above Step.

Preparation D: 4-Methyl-3-(4-methyl-1-piperazinyl)aniline

Step 1: 4-(2-Methylphenyl)-1-piperazinecarbaldehyde

With vigorous stirring, 437 mmol (77 g) of 2-methylphenylpiperazine are added to a solution of 415 mmol (61.3 g) of trichloroacetaldehyde in 400 ml of dibutyl ether. The reaction mixture is heated at 80° C. for 1 hour and, after cooling, concentrated to yield the expected product.

Step 2: 1-Methyl-4-(2-methylphenyl)piperazine

A solution of 437 mmol (90 g) of the compound described in the above Step in 400 ml of tetrahydrofuran is added to a suspension of 568 mmol (21.6 g) of lithium tetrahydroaluminate in 300 ml of tetrahydrofuran. The reaction mixture is stirred for 12 hours at 50° C. After cooling, the reaction mixture is hydrolysed with 52.5 ml of water and then 48 ml of an aqueous 10% sodium hydroxide solution and finally with 88.5 ml of water. The precipitate formed is filtered off over Celite and the filtrate is concentrated. The residue obtained is taken up in 200 ml of water and extracted 3 times with 250 ml of dichloromethane. The organic phase is dried over magnesium sulphate and concentrated to yield the expected product.

Step 3: 1-Methyl-4-(2-methyl-5-nitrophenyl)piperazine hydrochloride 416 mmol (64 g) of potassium nitrate in powder form are added to a solution of 347 mmol (100 g) of the hydrogen sulphate of the compound described in the above Step in 500 ml of concentrated sulphuric acid. Stirring is carried out for 5 hours, and the reaction mixture is poured onto 1200 g of ice and then neutralised with solid potassium carbonate and extracted 3 times with 500 ml of ethyl acetate. The organic phases are dried and concentrated to yield the expected product. The corresponding hydrochloride is obtained by the action of an ethanolic HCl solution.

Step 4: 4-Methyl-3-(4-methyl-1-piperazinyl)aniline

The expected product is obtained in accordance with the procedure described in Preparation A, Step 2, using as starting material the compound described in the above Step.

Preparation E: 3-[4-(2,3-Dihydro-1,4-benzodioxin-2-ylmethyl)-1-piperazinyl]aniline Step 1: 1-(2,3-Dihydro-1,4-benzodioxin-2-ylmethyl)-4-(3-nitrophenyl) piperazine A solution of 54.2 mmol (10 g) of 2-chloromethyl-2,3-dihydro-1,4-benzodioxin, 54.2 mmol (9.2 g) of 3-nitrophenylpiperazine and 6 g of potassium hydrogen carbonate in 100 ml of methyl-4-pentanone is heated at reflux for 72 hours. After cooling, the reaction mixture is concentrated. The residue is taken up in 200 ml of water and extracted with 200 ml of dichloromethane. The organic phase is dried over magnesium sulphate, concentrated and purified by chromatography on silica gel, using as eluant a 99/1/0.1 dichloromethane/methanol/ammonium hydroxide mixture, to yield the expected product.

Step 2: 3-[4-(2,3-Dihydro-1,4-benzodioxin-2-ylmethyl)-1-piperazinyl]aniline

The expected product is obtained in accordance with the procedure described in Preparation A, Step 2, using as starting material the compound described in the above Step.

Preparation F: $N^3$-(4,5-Dihydro-1H-imidazol-2-yl)-4-methyl-1,3-benzenediamine

Step 1: 2-Methyl-5-nitrophenylcarbamothioic acid chloride 2.25 l of water are added to a solution of 130 mmol (20 g) of 2-methyl-5-nitroaniline in 375 ml of concentrated hydrochloric acid. At a temperature of 0° C., 162 mmol (19 g) of thiophosgene are poured in in one go. The reaction mixture is stirred vigorously for 24 hours at ambient temperature. The precipitate formed is filtered off and then taken up in diethyl ether. The organic phase is washed with water, dried over magnesium sulphate and concentrated to yield the expected product.

Step 2: N-(2-Aminoethyl)-N'-(2-methyl-5-nitrophenyl) thiourea

A solution of 123 mmol (24 g) of the compound described in the above Step in 1000 ml of toluene is heated to 60° C. 246 mmol (8.27 ml) of ethylenediamine are rapidly added and the mixture is heated at 100° C. for 3 hours. After cooling, the organic phase is washed with a 1M hydrochloric acid solution. The aqueous phase is rendered alkaline with concentrated sodium hydroxide solution and then extracted with dichloromethane. The organic phase is washed with water, dried over magnesium sulphate, concentrated and purified by chromatography on silica gel, using as eluant a 90/10/1 dichloromethane/methanol/-ammonium hydroxide mixture, to yield the expected product.

Step 3: N-(2-Methyl-5-nitrophenyl)-4,5-dihydro-1H-imidazol-2-amine

A hot solution of 38.8 g of potassium hydroxide in 135 ml of water is added at 50° C. to a solution of 63 mmol (16.0 g) of the compound described in the above Step. With vigorous stirring, at 80° C., a hot solution of 72.5 mmol (27.2 g) of lead acetate in 135 ml of water is added. After 30 minutes, the reaction mixture is filtered over Celite and concentrated. The residue is taken up in 100 ml of water and the pH is adjusted to 10. Following extraction with dichloromethane, the organic phase is dried over magnesium sulphate and concentrated to yield the expected product.

Step 4: $N^3$-(4,5-Dihydro-1H-imidazol-2-yl)-4-methyl-1,3-benzenediamine

The expected product is obtained in accordance with the procedure described in Preparation A, Step 2, using as starting material the compound described in the above Step.

Preparation G: $N^1$-(4,5-Dihydro-1H-imidazol-2-yl)-1,3-benzenediamine

Step 1: N-(3-Nitrophenyl)-4,5-dihydro-1H-imidazol-2-amine

The expected product is obtained in accordance with the procedure described in Preparation F, Step 2, using as starting material 3-nitrophenyl isothiocyanate.

Step 2: $N^1$-(4,5-Dihydro-1H-imidazol-2-yl)-1,3-benzenediamine

The expected product is obtained in accordance with the procedure described in Preparation A, Step 2, using as starting material the compound described in the above Step.

Preparation H: 2-Methoxy-5-(4-methyl-1-piperazinyl)benzoyl azide

A solution of 25 mmol (5.3 g) of phenyl dichlorophosphate in 100 ml of dichloromethane is added to a solution of 20 mmol (5 g) of 4-methoxy-3-(4-methyl-1-piperazinyl) benzoic acid (described in J. Med. Chem., 1994, 37, p.2255) and 50 mmol (3.25 g) of sodium azide in 4.05 ml of pyridine. After stirring for 12 hours at ambient temperature, the organic phase is washed with 100 ml of water, dried over magnesium sulphate and concentrated to yield the expected product.

EXAMPLE 1

N-(3-Chloro-4-methylphenyl)-N'-[3-(4,5-dihydro-1H-imidazol-2-ylmethyl)phenyl]urea hydrochloride A solution of 4.7 mmol (1 g) of the compound described in Preparation A and 4.7 mmol (0.79 g) of 3-chloro-4-methylphenyl isocyanate in 50 ml of dimethylformamide is heated for 2 hours at 100° C. After cooling, the reaction mixture is concentrated. The residue obtained is taken up in 200 ml of dichloromethane, and the precipitate obtained is filtered off and purified by chromatography on silica gel, using as eluant a 90/10/1 dichloromethane/methanol/ammonia mixture, to yield the expected product. The corresponding hydrochloride is obtained by the action of an ethanolic HCl solution.

Melting point: 227–229° C. Elemental microanalysis: $C_{18}H_{19}ClN_4O.HCl$

|  | C | H | N | Cl |
|---|---|---|---|---|
| % Calculated: | 57.00 | 5.31 | 14.77 | 9.35 |
| % Found: | 56.56 | 5.41 | 14.32 | 9.59 |

EXAMPLE 2

N-(3-Chloro-4-methylphenyl)-N'-{3-[1-(4,5-dihydro-1H-imidazol-2-yl)ethyl]phenyl}urea hydrochloride The expected product is obtained in accordance with the procedure described in Example 1, with replacement of the product described in Preparation A with the compound described in Preparation B.

Melting point: 100–102° C. Elemental microanalysis: $C_{19}H_{21}ClN_4O.HCl$

|  | C | H | N | Cl |
|---|---|---|---|---|
| % Calculated: | 58.02 | 5.64 | 14.24 | 9.01 |
| % Found: | 58.07 | 5.95 | 13.55 | 8.91 |

EXAMPLE 3:

N-(3-Chloro-4-methylphenyl)-N'-{3-[1-(4, 5-dihydro-1H-imidazol-2-yl)-1-methylethyl]phenyl}urea hydrochloride The expected product is obtained in accordance with the procedure described in Example 1, with replacement of the product described in Preparation A with the compound described in Preparation C.

Melting point: 232–233° C. Elemental microanalysis: $C_{20}H_{23}ClN_4O.HCl$

|  | C | H | N | Cl |
|---|---|---|---|---|
| % Calculated: | 58.97 | 5.94 | 13.75 | 8.70 |
| % Found: | 58.32 | 6.11 | 13.13 | 9.11 |

EXAMPLE 4

N-(3-Chloro-4-methylphenyl)-N'-[4-methoxy-3-(4-methyl-1-piperazinyl)phenyl]urea hydrochloride A mixture of 13.6 mmol (3 g) of 4-methoxy-3-(4-methyl-1-piperazinyl)phenylamine and 13.6 mmol (2.26 g) of 3-chloro-4-methylphenyl isocyanate in 100 ml of toluene is heated at reflux for 2 hours. After cooling, the precipitate obtained is filtered off, and rinsed twice with diethyl ether. The solid obtained is purified by chromatography on silica gel, using as eluant a 96/4/0.4 dichloromethane/methanol/ammonium hydroxide mixture, to yield the expected product. The corresponding hydrochloride is obtained by the action of an ethanolic HCl solution.

Melting point: 206–208° C. Elemental microanalysis: $C_{20}H_{25}ClN_4O_2.HCl$

|  | C | H | N | Cl |
|---|---|---|---|---|
| % Calculated: | 55.29 | 6.10 | 12.90 | 18.36 |
| % Found: | 55.59 | 6.14 | 12.70 | 18.31 |

EXAMPLE 5

N-(3-Chloro-4-methylphenyl)-N'-[4-methyl-3-(4-methyl-1-piperazinyl)phenyl]urea hydrochloride The expected product is obtained using the procedure described in Example 4, with the replacement of 4-methoxy-3-(4-methyl-1-piperazinyl)phenylamine with the compound described in Preparation D.

Melting point : 229–231° C. Elemental microanalysis: $C_{20}H_{25}ClN_4O.HCl$

|  | C | H | N | Cl |
|---|---|---|---|---|
| % Calculated: | 58.68 | 6.40 | 13.69 | 17.32 |
| % Found: | 58.16 | 6.37 | 13.20 | 17.16 |

EXAMPLE 6

N-(3-Chloro-4-methylphenyl)-N'-{3-[4-(2,3-dihydro-1, 4-benzodioxin-2-ylmethyl)-1-piperazinyl]phenyl}urea hydrochloride The expected product is obtained using the procedure described in Example 4, with the replacement of 4-methoxy-3-(4-methyl-1-piperazinyl)phenylamine with the compound described in Preparation E.

Melting point: 180–185° C. Elemental microanalysis: $C_{27}H_{29}ClN_4O_3.HCl$

|  | C | H | N | Cl |
|---|---|---|---|---|
| % Calculated: | 57.30 | 5.53 | 9.90 | 18.79 |
| % Found: | 57.36 | 5.55 | 9.63 | 18.85 |

EXAMPLE 7

N-(3-Chloro-4-methylphenyl)-N'-[3-(4, 5-dihydro-1H-imidazol-2-ylamino)-4-methylphenyl]urea hydrochloride The expected product is obtained in accordance with the procedure described in Example 1, with replacement of the product obtained in Preparation A with the compound described in Preparation F.

Melting point: 252–254° C. Elemental microanalysis: $C_{18}H_{20}ClN_5O.HCl$

|  | C | H | N | Cl |
|---|---|---|---|---|
| % Calculated: | 54.83 | 5.37 | 17.76 | 8.99 |
| % Found: | 54.91 | 5.25 | 17.78 | 9.12 |

EXAMPLE 8

N-(3-Chloro-4-methylphenyl)-N'-[3-(4,5-dihydro-1H-imidazol-2-ylamino)phenyl]urea hydrochloride The expected product is obtained in accordance with the procedure described in Example 1, with replacement of the product described in Preparation A with the compound described in Preparation G.

Melting point: 180–185° C. Elemental microanalysis: $C_{17}H_{18}ClN_5O.HCl$

|  | C | H | N | Cl |
|---|---|---|---|---|
| % Calculated: | 53.01 | 5.10 | 18.14 | 10.38 |
| % Found: | 53.18 | 5.02 | 18.25 | 10.16 |

EXAMPLE 9

N-[4-Chloro-3-(4,5-dihydro-1H-imidazol-2-ylamino)phenyl]-N'-(3-chloro-4-methylphenyl) urea hydrochloride Step a: N-(3-Chloro-4-methylphenyl)-N'-(4-chloro-3-nitrophenyl)urea A solution of 29.8 mmol (5 g) of 3-chloro-4-methylphenyl isocyanate in 90 ml of toluene is heated to 70° C., and 29.8 mmol (5.15 g) of 4-chloro-3-nitroaniline are poured in. The solution is heated at reflux for 24 hours. The reaction mixture is cooled using ice, and the precipitate formed is filtered off and then rinsed with diethyl ether to yield the expected product.

Step b: N-(3-Amino-4-chlorophenyl)-N'-(3-chloro-4-methylphenyl)urea

A solution of 22.2 mmol (7.5 g) of the compound described in the above Step in 80 ml of a methanol/tetrahydrofuran mixture is heated to 45° C. in the presence of Raney nickel. While controlling the temperature, 33.3 mmol (1.61 ml) of hydrazine hydrate are added. The temperature is maintained at 45° C. for 30 minutes and a further 33.3 mmol (1.61 ml) of hydrazine hydrate is added. The mixture is stirred at reflux for 30 minutes. After cooling, the catalyst is filtered off and the filtrate is concentrated. The residue obtained is taken up in diethyl ether and washed to yield the expected product.

Step c: 2-Chloro-5-{[[(3-chloro-4-methylanilino)carbonyl]amino}phenylcarbamothioic acid chloride 3.2 mmol (0.25 ml) of thiophosgene are added at 5° C. to a suspension of 3.2 mmol (0.32 g) of calcium carbonate in a mixture of 15 ml of dichloromethane and 2.2 ml of water. At that temperature, 3.2 mmol (1 g) of the compound described in the above Step dissolved in dichloromethane are added. After the additon of 4.25 mmol (0.36 g) of sodium hydrogen carbonate, the reaction mixture is stirred for 15 minutes at ambient temperature. After filtration over Celite, the filtrate is decanted off and the organic phase is washed with water and then with a saturated aqueous solution of sodium chloride. After drying over magnesium sulphate and filtration, the filtrate is concentrated. The residue obtained is taken up in diethyl ether and washed to yield the expected product.

Step d: N-[3-({[(2-Aminoethyl)amino]carbothioyl}-amino)-4-chlorophenyl]-N'-(3-chloro-4-methylphenyl) urea 4.4 mmol (0.27 ml) of ethylenediamine are rapidly added to a solution, heated to 60° C., of 2.2 mmol (0.78 g) of the compound described in the above Step in 35 ml of toluene. The reaction mixture is heated at 100° C. for 3 hours. After cooling, the organic phase is washed with a 1N hydrochloric acid solution (10 ml). The aqueous phase is rendered alkaline with concentrated sodium hydroxide solution and then extracted with dichloromethane. The organic phase is washed with water, dried over magnesium sulphate, filtered and concentrated. The residue obtained is purified by chromatography on silica gel, using as eluant a 90/10/1 dichloromethane/methanol/ammonium hydroxide mixture, to yield the expected product.

Step e: N-[4-Chloro-3-(4,5-dihydro-1H-imidazol-2-ylamino) phenyl]-N'-(3-chloro-4-methylphenyl)urea A hot solution of 16.5 mmol (1.5 g) of potassium hydroxide in 5.5 ml of water is added to a solution of 1.5 mmol (0.63 g) of the compound described in the above Step in 10 ml of ethanol at 50° C. With vigorous stirring at 80° C., a hot solution of 1.72 mmol (1.1 g) of lead acetate in 5.5 ml of water is added. After 30 minutes, the mixture is filtered over Celite and the filtrate is concentrated. The residue is taken up in 5 ml of water, the pH is adjusted to 10 and extraction is carried out with dichloromethane. The organic phase is dried over magnesium sulphate, concentrated and purified by chromatography on silica gel, using as eluant a 90/10/1 dichloromethane/methanol/ammonium hydroxide mixture, to yield the expected product. The corresponding hydrochloride is obtained by the action of an ethanolic HCl solution.

Melting point: 255–257° C. Elemental microanalysis: $C_{17}H_{17}Cl_2N_5O \cdot HCl$

|  | C | H | N | Cl |
|---|---|---|---|---|
| % Calculated: | 49.23 | 4.37 | 16.89 | 25.65 |
| % Found: | 48.82 | 4.47 | 16.62 | 25.44 |

EXAMPLE 10

N-(3-Chloro-4-methylphenyl)-N'-{3-[4-(2,3-dihydro-1, 4-benzodioxin-2-ylmethyl)-1-piperazinyl]-4-methoxyphenyl}urea hydrochloride Step a: 4-(5-{[(3-Chloro-4-methylanilino)carbonyl] amino}-2-methoxyphenyl)-1-piperazinecarboxylic acid tert-butanolate A solution of 34.4 mmol (10 g) of 4-(5-amino-2-methoxyphenyl)piperazine-1-carboxylic acid tert-butanolate (described in J. Med. Chem., 1999, p.202) and 37.8 mmol (5.9 g) of 3-chloro-4-methylphenyl isocyanate in 150 ml of toluene is heated at reflux for 2 hours. The reaction mixture is concentrated, and the residue is taken up in 200 ml of 4N hydrochloric acid and then heated at reflux for 4 hours. After cooling, the precipitate formed is filtered off and treated with a 2N sodium hydroxide solution in order to regenerate the corresponding base.

Step b: N-(3-Chloro-4-methylphenyl)-N'-{3-[4-(2,3-dihydro-1, 4-benzodioxin-2-ylmethyl)-1-piperazinyl]-4-methoxyphenyl}urea A solution of 12.3 mmol (5 g) of the product described in the above Step in a mixture of 100 ml of acetonitrile and 100 ml of diethyl ketone is heated at reflux for 48 hours in the presence of 12.3 mmol (2.3 g) of 2-chloromethyl-2,3-dihydro-1,4-benzodioxin, 1.3 g of potassium hydrogen carbonate and 100 mg of potassium iodide. After cooling, the mixture is concentrated and the residue obtained is extracted with dichloromethane. The organic phase is dried, concentrated and purified by chromatography on silica gel, using as eluant a 97/3/0.3 dichloromethane/methanol/ammonium hydroxide mixture, to yield the expected product. The corresponding hydrochloride is obtained by the action of an ethanolic HCl solution.

Melting point: 193–197° C. Elemental microanalysis: $C_{28}H_{31}ClN_4O_4 \cdot HCl$

|  | C | H | N | Cl |
|---|---|---|---|---|
| % Calculated: | 58.23 | 5.88 | 9.58 | 7.29 |
| % Found: | 58.95 | 5.72 | 9.82 | 8.08 |

EXAMPLE 11

6-Chloro-5-fluoro-N-[4-methoxy-3-(4-methyl-1-piperazinyl)phenyl]-1-indolinecarboxamide A solution of 10.9 mmol (3 g) of the compound described in Preparation H in 100 ml of toluene is heated at reflux for 1 hour. After cooling to 20° C., a solution of 10.9 mmol (1.9 g) of 6-chloro-5-fluoroindoline in 200 ml of dichloromethane is added, and the reaction mixture is heated at reflux for one night. After returning to ambient temperature, the reaction mixture is concentrated and purified by chromatography on silica gel, using as eluant a 95/5/0.5 dichloromethane/methanol/ammonium hydroxide mixture, to yield the expected product.

Melting point: 177–180° C. Elemental microanalysis: $C_{21}H_{24}ClFN_4O_2$

|  | C | H | N | Cl |
|---|---|---|---|---|
| % Calculated: | 60.21 | 5.77 | 13.37 | 8.46 |
| % Found: | 59.15 | 6.05 | 12.82 | 8.85 |

EXAMPLE 12

N-{3-[4-(2,3-dihydro-1,4-benzodioxin-2-ylmethyl)-1-piperazinyl]phenyl}-1,2-dihydro-3H-benzo[e]indole-3-carboxamide dihydrochloride 20 ml of a solution of 20% by weight phosgene in toluene are added at 20° C. to a solution of 3.12 g of 1,2-dihydrobenzo[e]indole in 300 ml of toluene. After one hour at 50° C., the mixture is heated to 100° C. with bubbling with nitrogen. A solution in toluene of 6 g of the compound described in Preparation E is then added at 20° C., and the mixture is subsequently heated at 80° C. for 12 hours. Following treatment, the residue is purified by chromatography on silica gel, using as eluant a 99/1/0.1 dichloromethane/methanol/-ammonium hydroxide mixture.

The corresponding dihydrochloride is obtained by the action of an ethanolic HCl solution.

Melting point: 194–196° C. Elemental microanalysis: $C_{32}H_{32}N_4O_3 \cdot 2HCl$

|  | C | H | N | Cl |
|---|---|---|---|---|
| % Calculated: | 64.75 | 5.79 | 9.44 | 11.95 |
| % Found: | 65.17 | 5.75 | 9.46 | 10.88 |

EXAMPLE 13

6-Chloro-5-fluoro-N-{3-[4-(2, 3-dihydro-1,4-benzodioxin-2-ylmethyl)-1-piperazinyl]-phenyl}-1-2,3-dihydroindolecarboxamide dihydrochloride The expected product is obtained using the procedure described in Example 12, with the replacement of 1,2-dihydrobenzo[e]indole with 6-chloro-5-fluoro-2,3-dihydroindole.

Melting point: 202–204° C. Elemental microanalysis: $C_{28}H_{28}ClFN_4O_3.2HCl$

| | C | H | N | Cl |
|---|---|---|---|---|
| % Calculated: | 56.43 | 5.07 | 9.40 | 17.85 |
| % Found: | 56.22 | 4.92 | 9.40 | 17.98 |

EXAMPLE 14

N-{3-[4-(2,3-Dihydro-1, 4-benzodioxin-2-ylmethyl)-1-piperazinyl]-4-methoxyphenyl}-N'-(3,4-dimethylphenyl)urea dihydrochloride Step 1: 1-(2,3-Dihydrobenzo[1,4]dioxin-2-ylmethyl)-4-(2-methoxy-5-nitro-phenyl)piperazine The expected product is obtained using the procedure described in Preparation E, with the replacement of 3-nitrophenylpiperazine with 2-methoxy-5-nitrophenylpiperazine.

Step 2: 3-[4-(2,3-Dihydrobenzo[1,4]dioxin-2-ylmethyl)-piperazin-1-yl]-4-methoxyphenylamine The expected product is obtained using the procedure described in Preparation A, Step 2, using as starting material the compound described in the above Step.

Step 3: N-{3-[4-(2,3-Dihydro-1, 4-benzodioxin-2-ylmethyl)-1-piperazinyl]-4-methoxyphenyl}-N'-(3,4-dimethylphenyl) urea dihydrochloride The final product is then obtained using the procedure described in Example 4, with the replacement of 4-methoxy-3-(4-methyl-1-piperazinyl)phenylamine with the compound described in Step 2 of that Example and with the replacement of 3-chloro-4-methylphenyl isocyanate with 3,4-dimethylphenyl isocyanate.

Melting point: 234–236° C. Elemental microanalysis: $C_{29}H_{34}N_4O_4.2HCl$

| | C | H | N | Cl |
|---|---|---|---|---|
| % Calculated: | 60.52 | 6.30 | 9.73 | 12.32 |
| % Found: | 60.50 | 6.23 | 9.79 | 12.12 |

EXAMPLE 15

N-(3-Chloro-4-fluorophenyl)-N'-{3-[4-(2,3-dihydro-1, 4-benzodioxin-2-ylmethyl)-1-piperazinyl]-4-methoxyphenyl}urea hydrochloride The expected product is obtained using the procedure described in Example 14, with the replacement of 3,4-dimethylphenyl isocyanate with 3-chloro-4-fluorophenyl isocyanate.

Melting point: 120–130° C. Elemental microanalysis: $C_{27}H_{28}ClFN_4O_4.HCl$

| | C | H | N | Cl |
|---|---|---|---|---|
| % Calculated: | 57.56 | 5.19 | 9.94 | 12.58 |
| % Found: | 57.62 | 5.39 | 9.59 | 11.72 |

EXAMPLE 16

N-{3-[4-(2,3-Dihydro-1,4-benzodioxin-2-ylmethyl)-1-piperazinyl]phenyl}-N'-(3,4-dimethylphenyl)urea hydrochloride The expected product is obtained using the procedure described in Example 4, with the replacement of 4-methoxy-3-(4-methyl-1-piperazinyl)phenylamine with the compound described in Preparation E and using 3,4-dimethylphenyl isocyanate instead of 3-chloro-4-methylphenyl isocyanate.

Melting point: 228–230° C. Elemental microanalysis: $C_{28}H_{32}N_4O_3.HCl$

| | C | H | N | Cl |
|---|---|---|---|---|
| % Calculated: | 66.07 | 6.53 | 11.01 | 6.96 |
| % Found: | 65.80 | 6.50 | 10.96 | 7.37 |

EXAMPLE 17

N-(3-Chloro-4-fluorophenyl)-N'-{3-[4-(2,3-dihydro-1, 4-benzodioxin-2-ylmethyl)-1-piperazinyl]phenyl}urea hydrochloride The expected product is obtained using the procedure described in Example 4, with the replacement of 4-methoxy-3-(4-methyl-1-piperazinyl)phenylamine with the compound described in Preparation E and using 3-chloro-4-fluorophenyl isocyanate instead of 3-chloro-4-methylphenyl isocyanate.

Melting point: 132–136° C. Elemental microanalysis: $C_{26}H_{26}ClFN_4O_3.HCl$

| | C | H | N | Cl |
|---|---|---|---|---|
| % Calculated: | 58.54 | 5.10 | 10.50 | 13.29 |
| % Found: | 58.40 | 5.47 | 10.02 | 12.61 |

EXAMPLE 18

6-Chloro-5-methyl-N-{4-[4-(2,3-dihydro-1, 4-benzodioxin-2-ylmethyl)-1-piperazinyl]phenyl}-1-2,3-dihydroindolecarboxamide dihydrochloride The expected product is obtained using the procedure described in Example 12, with the replacement of 1,2-dihydrobenzo[e]indole with 6-chloro-5-methyl-2,3-dihydroindole.

Melting point: 174–176° C. Elemental microanalysis: $C_{29}H_{31}ClN_4O_3.2HCl$

| | C | H | N | Cl |
|---|---|---|---|---|
| % Calculated: | 58.84 | 5.62 | 9.46 | 17.97 |
| % Found: | 58.77 | 5.46 | 9.16 | 18.82 |

EXAMPLE 19

N-(3-Chloro-4-methylphenyl)-N'-[2-(1H-imidazol-4-yl)-indan-5-yl]urea hydrochloride Step 1: 2-Bromo-1-indan-2-ylethanone 10 g of pure bromine are rapidly added at 0° C. to a solution of 10 g of 2-acetylindane in 150 ml of anhydrous methanol. After one hour at ambient temperature, 100 ml of water are added and the whole is stirred for 12 hours. After extracting twice with 200 ml of diethyl ether each time, and washing the organic phase with a sodium hydrogen carbonate solution and then with water, the expected product is dried over magnesium sulphate and concentrated.

Step 2: 4-Indan-2-yl-1H-imidazole

A mixture of 5.2 g of 2-bromo-1-indan-2-ylethanone and 43.4 ml of formamide is heated at 160° C. for 30 minutes. At ambient temperature 40 ml of water and then 40 ml of 1N hydrochloric acid are added. The aqueous phase is washed with dichloromethane and then neutralised with ammonium hydroxide. Extraction with ethyl acetate yields the expected product after evaporation.

Step 3: 4-(5-Nitroindan-2-yl)-1H-imidazole 5 g of 4-indan-2-yl-1H-imidazole are dissolved at 0° C. in 140 ml of pure sulphuric acid, and then 1 equivalent of urea nitrate in powder form is added in small portions. The reaction mixture is poured onto ice, rendered alkaline using sodium hydroxide solution and extracted with ethyl acetate. The expected product is obtained after evaporation.

Step 4: 2-(1H-Imidazol-4-yl)-indan-5-ylamine

The hydrochloride of the product obtained in Step 3 is stirred under a hydrogen atmosphere in the presence of 10% palladium-on-carbon in ethanol. After filtration and concentration of the solvent, the product is used as it is in the following Step.

Step 5: N-(3-Chloro-4-methylphenyl)-N'-[2-(1H-imidazol-4-yl)-indan-5-yl]urea hydrochloride A mixture of 5.3 g of the hydrochloride of the product obtained in Step 4, 3.8 g of 3-chloro-4-methylphenyl isocyanate and 150 ml of dimethylformamide is heated at 100° C. for 2 hours. After subsequent evaporation of the solvent, the residue is purified by chromatography on silica gel using as eluant a 97/3/0.3 dichloromethane/methanol/-ammonium hydroxide mixture.

The corresponding hydrochloride is obtained by the action of an ethanolic HCl solution.

Melting point: 235–237° C. Elemental microanalysis: $C_{20}H_{19}ClN_4O.1HCl$

|  | C | H | N | Cl |
|---|---|---|---|---|
| % Calculated: | 59.56 | 5.00 | 13.89 | 17.58 |
| % Found: | 58.95 | 5.17 | 13.36 | 17.01 |

EXAMPLE 20

N-[2-(1H-Imidazol-4-yl)indan-5-yl]-N'-(4-methylsulphanylphenyl) urea hydrochloride The expected product is obtained using the procedure described in Example 19, with the replacement of 3-chloro-4-methylphenyl isocyanate with 4-methylthiophenyl isocyanate.

Melting point: 243–245° C. Elemental microanalysis: $C_{20}H_{20}N_4OS.HCl$

|  | C | H | N | Cl | S |
|---|---|---|---|---|---|
| % Calculated: | 59.92 | 5.28 | 13.97 | 8.84 | 8.00 |
| % Found: | 59.72 | 5.32 | 13.26 | 8.56 | 7.73 |

EXAMPLE 21

N-(3,4-Dimethylphenyl)-N'-[2-(1H-imidazol-4-yl)-indan-5-yl]urea hydrochloride

The expected product is obtained using the procedure described in Example 19, with the replacement of 3-chloro-4-methylphenyl isocyanate with 3,4-dimethylphenyl isocyanate.

Melting point: 232–234° C. Elemental microanalysis: $C_{21}H_{22}N_4O.HCl$

|  | C | H | N | Cl |
|---|---|---|---|---|
| % Calculated: | 65.88 | 6.05 | 14.63 | 9.26 |
| % Found: | 65.47 | 6.30 | 14.29 | 9.29 |

EXAMPLE 22

N-(3-Chloro-4-methylphenyl)-N'-[2-(4,5-dihydro-1H-imidazol-2-yl)-1, 2,3,4-tetrahydro-7-isoquinolinyl]urea hydrochloride Step 1: 2-(4,5-Dihydro-1H-imidazol-2-yl)-7-nitro-1,2,3,4-tetrahydro-isoquinoline A mixture of 10 g of 7-nitro-1,2,3,4-tetrahydroisoquinoline, 13.7 g of 2-methylsulphanyl-4,5-dihydro-1H-imidazole hydriodide and 100 ml of methanol is heated at reflux for 12 hours. The addition of diethyl ether causes the separation of a precipitate, which is taken up in water, neutralised using sodium hydroxide and extracted with dichloromethane.

Step 2: 2-(4,5-Dihydro-1H-imidazol-2-yl)-1,2,3,4-tetrahydroisoquinolin-7-ylamine 2 ml of hydrazine hydrate are added at 40° C. to a suspension of 2 g of the hydrochloride of the product obtained in Step 1 and 2 g of Raney nickel in 50 ml of ethanol. After 2 hours at 50° C., the catalyst is filtered off and the solvent is evaporated off.

Step 3: N-(3-Chloro-4-methylphenyl)-N'-[2-(4,5-dihydro-1H-imidazol-2-yl)-1, 2,3,4-tetrahydro-7-isoquinolinyl]urea hydrochloride The expected product is obtained using the procedure described in Step 5 of Example 19.

Melting point: 237–239° C. Elemental microanalysis: $C_{20}H_{22}ClN_5O.HCl$

|  | C | H | N | Cl |
|---|---|---|---|---|
| % Calculated: | 57.09 | 5.47 | 16.65 | 16.89 |
| % Found: | 57.41 | 5.51 | 16.32 | 16.74 |

EXAMPLE 23

N-(3-Chloro-4-methylphenyl)-N'-{3-[2-(1H-imidazol-4-yl)ethyl]-phenyl}urea hydrochloride Step 1: (3-Nitrophenyl)acetaldehyde A mixture of 10 g of 2-(3-nitrophenyl)ethanol, 25.1 g of 1-hydroxy-1,2-benziodoxol-3(1H)-one 1-oxide and 300 ml of tetrahydrofuran is heated at reflux for 6 hours. After filtration and concentration of the solvent, the product is used as it is in the following Step.

Step 2: 2-(3-Nitrophenyl)-1-(1-trityl-1H-imidazol-4-yl)-ethanol

At ambient temperature, 4.2 ml of 3M ethylmagnesium bromide are poured into 5.48 g of 4-iodo-1-trityl-1H-imidazole dissolved in 30 ml of dichloromethane. After 1 hour, 1 g of the product obtained in Step 1 is dissolved in 20 ml of dichloromethane. After hydrolysis with a saturated solution of ammonium chloride, extraction with dichloromethane, and then washing the organic phase with water, the solvent is evaporated off and the residue is purified by chromatography on silica gel, using as eluant a 98/2 dichloromethane/methanol mixture.

Step 3: 4-[2-(3-Nitrophenyl)vinyl]-1-trityl-1H-imidazole

A mixture of 12.25 g of the product obtained in Step 2, 1 g of para-toluenesulphonic acid and 200 ml of toluene is heated at reflux for 5 hours. After returning to ambient temperature, washing the toluene solution with a 0.1N solution of sodium hydroxide and then with water, drying over magnesium sulphate and concentration, the expected product is obtained.

Step 4: 4-[2-(3-Nitrophenyl)vinyl]-1H-imidazole

A mixture of 11 g of the product obtained in Step 3, 6 ml of concentrated hydrochloric acid and 150 ml of methanol is heated at reflux for 2 hours. The solvent is concentrated and the residue is taken up in an isopropanol/diethyl ether mixture. The expected product is obtained by filtering off the precipitate that has formed.

Step 5: 3-[2-(1H-Imidazol-4-yl)ethyl]phenylamine

The hydrochloride of the product obtained in Step 4 is stirred under a hydrogen atmosphere in the presence of a 90% solution of 10% palladium-on-carbon in ethanol. After filtration and concentration of the solvent, the product is used as it is in the following Step.

Step 6: N-(3-Chloro-4-methylphenyl)-N'-{3-[2-(1H-imidazol-4-yl)-ethyl]-phenyl}urea hydrochloride The expected product is obtained using the procedure described in Step 5 of Example 19.

Melting point: 237–239° C. Elemental microanalysis: $C_{19}H_{19}ClN_4O.HCl$

|  | C | H | N | Cl |
|---|---|---|---|---|
| % Calculated: | 58.32 | 5.15 | 14.32 | 18.12 |
| % Found: | 58.40 | 5.13 | 13.97 | 18.35 |

EXAMPLE 24

N-(3-Chloro-4-methylphenyl)-N'-{3-[2-(4,5-dihydro-1H-imidazol-2-yl)ethyl]phenyl}urea hydrochloride Step 1: 3-(3-Nitrophenyl)acrylonitrile At 0° C., 75.5 g of diethyl cyanomethylphosphonate dissolved in tetrahydrofuran are poured into a suspension of sodium hydride in tetrahydrofuran. After 30 minutes' contact at ambient temperature, 56 g of 3-nitrobenzaldehyde dissolved in tetrahydrofuran are poured in. After 1 hour, hydrolysis is carried out with 300 ml of water and then the solvent is concentrated. Following extraction with dichloromethane, washing the organic phase with water, drying over magnesium sulphate and concentration, the precipitate is taken up in diethyl ether and filtered off.

Step 2: 3-(3-Nitrophenyl)propionitrile

There are introduced into a cylinder 3 g of the product obtained in Step 1, 1.59 g of tris(triphenylphosphine)rhodium(I) chloride and 90 ml of benzene. The whole is heated for 5 hours at 40° C. under a hydrogen pressure of 5 bar. The solvent is evaporated off and the residue is purified by chromatography on silica gel using dichloromethane as eluant.

Step 3: 2-[2-(3-Nitrophenyl)ethyl]-4,5-dihydro-1H-imidazole 1 g of the product obtained in Step 2 is heated for 2 hours at 160° C. with 1.32 g of ethylenediamine para-toluenesulphonate. A 0.1N sodium hydroxide solution is then added and extraction is carried out with dichloromethane. The organic phase is washed with water, dried over magnesium sulphate and concentrated. The corresponding hydrochloride is obtained by the action of an ethanolic HCl solution.

Step 4: 3-[2-(4,5-Dihydro-1H-imidazol-2-yl)ethyl]phenylamine

The hydrochloride of the product obtained in Step 3 is stirred under a hydrogen atmosphere in the presence of a 90% solution of 10% palladium-on-carbon in ethanol. After filtration and concentration of the solvent, the product is used as it is in the following Step.

Step 5: N-(3-Chloro-4-methylphenyl)-N'-{3-[2-(4,5-dihydro-1H-imidazol-2-yl) ethyl]phenyl}urea hydrochloride The expected product is obtained using the procedure described in Step 5 of Example 19.

Melting point: 212–214° C. Elemental microanalysis: $C_{19}H_{21}ClN_4O.HCl$

|  | C | H | N | Cl |
|---|---|---|---|---|
| % Calculated: | 58.02 | 5.64 | 14.24 | 18.03 |
| % Found: | 57.88 | 5.69 | 13.98 | 17.93 |

EXAMPLE 25

N-(3-Chloro-4-methylphenyl)-N'-[8-(1H-imidazol-4-yl)-5,6,7, 8-tetrahydro-2-naphthalenyl]urea hydrochloride Step 1: Trifluoromethanesulphonic acid 7-nitro-3,4,4a,8a-tetrahydro-naphthalen-1-yl ester 9.8 ml of trifluoromethanesulphonic anhydride are poured at 0° C. into a solution of 10 g of 7-nitrotetralone and 11.8 g of 2,6-di-tert-butyl-4-methylpyridine in 365 ml of dichloromethane. After 24 hours at ambient temperature, concentration to dryness and taking up the residue in 200 ml of pentane at reflux for 30 minutes, the precipitate formed is filtered off. The organic phase is washed with a 1N hydrochloric acid solution and then with water, dried over magnesium sulphate and concentrated.

Step 2: 4-(7-Nitro-3,4,4a,8a-tetrahydronaphthalen-1-yl)-1-trityl-1H-imidazole

At ambient temperature, 15.34 ml of 3M ethylmagnesium bromide are poured into 16.74 g of 4-iodo-1-trityl-1H-imidazole dissolved in 250 ml of tetrahydrofuran. After 1 hour, 76.6 ml of a 1N solution of zinc chloride in diethyl ether are poured in. After contact for 1 hour, 12.4 g of the product obtained in Step 1 dissolved in 100 ml of tetrahydrofuran and 2.22 g of tetrakis(triphenylphosphine)palladium(0) are added and the whole is heated at reflux. Following hydrolysis with a saturated solution of ammonium chloride and extraction with dichloromethane, the organic phase is washed with water. The solvent is then evaporated off and the residue is purified by chromatography on silica gel using as eluant an 80/20 cyclohexane/ethyl acetate mixture.

Step 3: 8-(1-Trityl-1H-imidazol-4-yl)-4a,5,6,7,8,8a-hexahydronaphthalen-2-ylamine 7.7 g of the product obtained in Step 2 are stirred under a hydrogen atmosphere in the presence of 10% palladium-on-carbon in a methanol/tetrahydrofuran mixture. After filtration and concentration of the solvent, the product is used as it is in the following Step.

Step 4: 8-(1H-Imidazol-4-yl)-4a,5,6,7,8,8a-hexahydronaphthalen-2-ylamine

A mixture of 7.7 g of the product obtained in Step 3, 4.2 ml of concentrated hydrochloric acid and 100 ml of methanol is heated at reflux for 2 hours. After concentration of the solvent, the residue is taken up in an isopropanol/diethyl ether mixture. The expected product is obtained by filtering off the precipitate.

Step 5: N-(3-Chloro-4-methylphenyl)-N'-[8-(1H-imidazol-4-yl)-5,6,7, 8-tetrahydro-2-naphthalenyl]urea hydrochloride A mixture of 0.7 g of the product obtained in Step 4, 0.55 g of 3-chloro-4-methylphenyl isocyanate and 50 ml of toluene is heated at reflux for 3 hours. The precipitate is then filtered off.

The corresponding hydrochloride is obtained by the action of an ethanolic HCl solution.

Melting point: 255–257° C. Elemental microanalysis: $C_{21}H_{21}ClN_4O.1HCl$

|  | C | H | N | Cl |
|---|---|---|---|---|
| % Calculated: | 60.44 | 5.31 | 13.42 | 16.99 |
| % Found: | 60.28 | 5.41 | 13.02 | 17.20 |

EXAMPLE 26

N-(3-Chloro-4-methylphenyl)-N'-[7-(1H-imidazol-4-yl)-5,6,7, 8-tetrahydro-2-naphthalenyl]urea hydrochloride Step 1: 7-Nitro-3,4-dihydro-1H-naphthalen-2-one At 0° C., 100 g of 2-tetralone are dissolved in 460 ml of pure sulphuric acid and 84.6 g of potassium nitrate in powder form are added in small portions. The mixture is then poured onto ice and extracted using dichloromethane. Following evaporation of the solvent, the residue is purified by chromatography on silica gel using as eluant a 90/10 cyclohexane/tetrahydrofuran mixture.

Step 2: Trifluoromethanesulphonic acid 7-nitro-3,4-dihydronaphthalen-2-yl ester

The expected product is obtained using the procedure described in Step 1 of Example 25, with the replacement of 7-nitrotetralone with 14.3 g of the product obtained in Step 1.

Step 3: 4-(7-Nitro-3,4-dihydronaphthalen-2-yl)-1-trityl-1H-imidazole

The expected product is obtained using the procedure described in Step 2 of Example 25, with the replacement of trifluoromethanesulphonic acid 7-nitro-3,4,4a,8a-tetrahydro-naphthalen-1-yl ester with 11.2 g of the product obtained in Step 2.

Step 4: 7-(1-Trityl-1H-imidazol-4-yl)-5,6,7,8-tetrahydronaphthalen-2-ylamine 5.5 g of the product obtained in Step 3 are stirred under a hydrogen atmosphere in a methanol/tetrahydrofuran mixture in the presence of 10% palladium-on-carbon. After filtration and concentration of the solvent, the product is used as it is in the following Step.

Step 5: 7-(1H-Imidazol-4-yl)-5,6,7,8-tetrahydronaphthalen-2-ylamine

A mixture of 5.5 g of the product obtained in Step 4, 3.8 ml of concentrated hydrochloric acid and 100 ml of methanol is heated at reflux for 2 hours. Following concentration of the solvent, the residue is taken up in an acetone/diethyl ether mixture. The precipitate is filtered off and yields the expected product.

Step 6: N-(3-Chloro-4-methylphenyl)-N'-[7-(1H-imidazol-4-yl)-5,6,7, 8-tetrahydro-2-naphthalenyl]urea hydrochloride A mixture of 0.9 g of the product obtained in Step 4, 0.71 g of 3-chloro-4-methylphenyl isocyanate and 70 ml of toluene is heated at reflux for 3 hours. The precipitate is filtered off and then recrystallised from an ethanol/methanol mixture.

The corresponding hydrochloride is obtained by the action of an ethanolic HCl solution.

Melting point: 206–208° C. Elemental microanalysis: $C_{21}H_{21}ClN_4O.1HCl$

|  | C | H | N | Cl |
|---|---|---|---|---|
| % Calculated: | 60.44 | 5.31 | 13.42 | 16.99 |
| % Found: | 59.84 | 5.17 | 13.06 | 16.88 |

EXAMPLE 27

N-(3-Chloro-4-methylphenyl)-N'-[4-(1H-imidazol-4-yl)-chroman-6-yl]urea hydrochloride Step 1: 6-Nitrochroman-4-one At −35° C., 60 g of 4-chromanone are added in small portions to 385 ml of 90% nitric acid. The whole is poured onto ice and then extracted with dichloromethane. The organic phase is washed with a saturated solution of sodium hydrogen carbonate and dried over magnesium sulphate and then the solvent is evaporated off.

Step 2: Trifluoromethanesulphonic acid 6-nitro-2H-chromen-4-yl ester

The expected product is obtained using the procedure described in Step 1 of Example 25, with the replacement of 7-nitrotetralone with 20 g of the product obtained in Step 1.

Step 3: 4-(6-Nitro-2H-chromen-4-yl)-1-trityl-1H-imidazole

The expected product is obtained using the procedure described in Step 2 of Example 25, with the replacement of trifluoromethanesulphonic acid 7-nitro-3,4,4a,8a-tetrahydro-naphthalen-1-yl ester with 11.1 g of the product obtained in Step 2.

Step 4: 4-(1H-Imidazol-4-yl)-chroman-6-ylamine

The hydrochloride of the product obtained in Step 3 is stirred under a hydrogen atmosphere in ethanol in the presence of 10% palladium-on-carbon. After filtration and concentration of the solvent, the product is used as it is in the following Step.

Step 5: N-(3-Chloro-4-methylphenyl)-N'-[4-(1H-imidazol-4-yl)-chroman-6-yl]urea hydrochloride A mixture of 0.76 g of the product obtained in Step 4, 0.59 g of 3-chloro-4-methylphenyl isocyanate and 70 ml of toluene is heated at reflux for 2 hours. The precipitate is filtered off and then recrystallised from an ethanol/methanol mixture.

The corresponding hydrochloride is obtained by the action of an ethanolic HCl solution.

Melting point: >260° C. Elemental microanalysis : $C_{20}H_{19}ClN_4O_2.1HCl$

|           | C     | H    | N     | Cl    |
|-----------|-------|------|-------|-------|
| % Calculated: | 57.29 | 4.81 | 13.36 | 16.91 |
| % Found:  | 56.83 | 4.98 | 12.96 | 16.63 |

Examples 28 to 30 were prepared in accordance with the procedures described above.

EXAMPLE 28

N-[3-(1H-Imidazol-4-yl)-chroman-6-yl]-1,2-dihydro-3H-benzo [e]indole-3-carboxamide

EXAMPLE 29

N-(3-Chloro-4-methylphenyl)-N'-[3-(1H-imidazol-4-yl)-chroman-6-yl]urea

EXAMPLE 30

N-(3-Chloro-4-methylphenyl)-N'-[2-(1H-imidazol-4-yl)-1,2,3,4-tetrahydro-7-isoquinolinyl]urea Pharmacological Study Example A Penile Erection Test in the Rat The test allows the evaluation of the capacity of pharmacological agents to inhibit penile erections caused by the administration of a 5-$HT_{2c}$ selective agonist, RO 60-0175.

Male Wistar rats weighing from 120 to 140 g on the day of the experiment are placed individually into plexiglass observation boxes immediately after having been administered the test compound or the carrier. Thirty minutes later, the animals are administered RO 60-0175 (1.25 mg/kg, subcutaneous route) and the number of erections that occur during the 30 minutes that follow is counted.

Results: The compounds of the invention appear to be capable of inhibiting penile erections induced by the administration of the 5-$HT_{2c}$ selective agonist. They accordingly have an antagonist character in respect of 5-$HT_{2c}$ receptors. By way of example, the inhibitory concentration 50 ($IC_{50}$) of the compound of Example 6 is 0.7 mg/kg.

Example B

Test in the Mouse of Aggressiveness Induced by Isolation

The animals used are male CD-1 mice. On arrival, the mice are isolated in individual cages with free access to food and drink. After a period of isolation of one month, pairs of mice that are constant in their aggressiveness are selected by observation of the latent period, the number and the duration of attacks when they are placed in each other's presence.

The test takes place once a week. On the day of the test, each mouse of the pair of mice (resident mouse and intruder mouse) is given a subcutaneous injection of carrier (control animals) or of test product (treated animals) in a volume of 10 ml/kg. After 30 minutes, the intruder mouse is introduced into the cage of the resident mouse. The latent period of the first attack and the number and duration of attacks are then measured for a period of three minutes.

A product is considered as specifically anti-aggressive when it reduces the number and the duration of attacks at non-sedative doses.

Results: The compounds of the invention appear to reduce significantly the number and duration of attacks. By way of example, the inhibitory dose 50 ($ID_{50}$) of the compound of Example 6 is 2.5 mg/kg (subcutaneous administration).

Example C

Marble-burying Test in the Mouse

This test allows evaluation of the capacity of pharmacological agents to inhibit the spontaneous marble-burying behaviour in mice, the inhibition being predictive of antidepressant and/or anti-impulsive action.

Male NMRI mice weighing from 20 to 25 g on the day of the experiment are placed individually in Macrolon boxes containing 5 cm of sawdust and covered with a perforated plexiglass plate. Twenty four "tiger's eye" glass marbles are evenly distributed on the sawdust at the periphery of the box. At the end of 30 minutes' free exploration, the animals are removed from the box and the number of buried marbles is counted.

Results : The compounds of the invention appear to inhibit spontaneous marble-burying behaviour in mice. By way of example, the effective dose 50 ($ED_{50}$) of the compound of Example 6 is 0.4 mg/kg.

Example D

Determination of the Affinity for $\alpha_2$ Adrenergic Receptors in the Rat

The affinity was determined by competition experiments with [$^3$H]-RX 821,002. Membranes are prepared from rat cerebral cortex and incubated in triplicate for 60 minutes at 22° C. with 0.4 nM [$^3$H]-RX 821,002 and the test compound in a final volume of 1.0 ml. The incubation buffer contains 50 nM Tris-HCl (pH 7.5), 1 mM EDTA and 100 µM GppNHp. Non-specific binding is determined using 10 µM phentolamine.

Data analysis: At the end of the incubation, the incubation medium is filtered across WHATMAN GF/B filters impregnated with 0.1% polyethylenimine and washed three times with 5 ml of cooled buffer. The radioactivity retained on the filters is determined by liquid scintillation counting. The binding isotherms are analysed by non-linear regression.

Results: The compounds of the invention exhibit an antagonist activity specific for $\alpha_2$-adrenergic receptors, for example a pKi of 6.7 for the compound of Example 6.

Example E

Pharmaceutical Composition

Formulation for the preparation of 1000 tablets each containing 10 mg of active ingredient

| compound of Example 6 | 10 g |
|---|---|
| hydroxypropyl cellulose | 2 g |
| wheat starch | 10 g |
| lactose | 100 g |
| magnesium stearate | 3 g |
| talc | 3 g |

We claim:

1. A compound selected from those of formula (I):

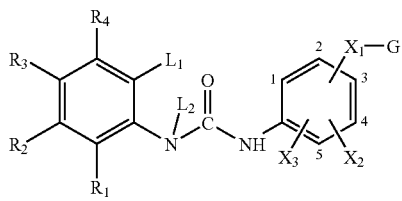

wherein
$R_1$, $R_2$, $R_3$ and $R_4$ independently represent hydrogen, halogen or alkyl, alkoxy, hydroxy, alkylthio, mercapto, cyano, amino (optionally substituted by one or two alkyl), nitro, carboxy, alkoxycarbonyl, aminocarbonyl (optionally substituted by one or two alkyl) or carbamoyl,
or, taken in pairs, form together with the carbon atoms to which they are bonded a phenyl ring or an aromatic heterocycle having from 5 to 6 ring members and containing from 1 to 3 hetero atoms selected from nitrogen, oxygen and sulphur,
$L_1$ and $L_2$ each represents hydrogen or together form —$CH_2$—$CH_2$—,
$X_1$, attached at the 2 or 3 position of the aromatic ring, represents a bond, and in that case $X_2$ represents hydrogen, halogen, alkyl, alkoxy, hydroxy, nitro or cyano, or amino (optionally substituted by one or two alkyl), or,
$X_1$ and $X_2$, together with two adjacent carbon to which they are bonded in the 2, 3 or 4 position of the aromatic ring, form ($C_4$–$C_7$)cycloalkyl wherein one or two —$CH_2$— of the cycloalkyl ring are optionally replaced by oxygen or NH (optionally substituted by alkyl) and wherein one carbon of the cycloalkyl ring is substituted by G,
$X_3$ represents hydrogen, halogen, alkyl, alkoxy, hydroxy, nitro or cyano, or amino (optionally substituted by one or two alkyl),
G represents a group selected from:

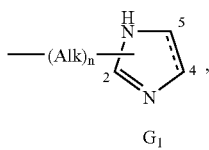 , 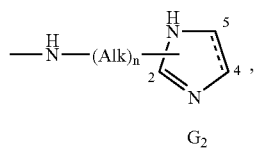 , $G_1$ $G_2$ wherein:
the broken lines indicate the optional presence of a double bond,
Alk represents linear or branched ($C_1$–$C_6$)alkylene wherein, when $G_1$ or $G_2$ contains imidazoline, the group Alk- is attached at the 2 position of the ring,
n is 0 or 1,
wherein:
the term "alkyl" denotes linear or branched group containing from 1 to 6 carbon,
the term "alkoxy" denotes linear or branched alkyl-oxy containing from 1 to 6 carbon, enantiomers and diastereoisomers thereof, and addition salts thereof with a pharmaceutically acceptable acid or base.

2. A compound of claim 1, wherein $L_1$ and $L_2$ each represents hydrogen.

3. A compound of claim 1, wherein $L_1$ and $L_2$ together form —$CH_2$—$CH_2$—.

4. A compound of claim 1, wherein $R_1$ and $R_4$ each represents hydrogen.

5. A compound of claim 1, wherein $R_2$ and $R_3$ are selected from halogen and alkyl.

6. A compound of claim 1, wherein $X_1$ is attached at the 2 position of the phenyl ring.

7. A compound of claim 1, wherein $X_1$ represents a bond and $X_2$ represents halogen or alkyl or alkoxy.

8. A compound of claim 1, wherein $X_3$ represents hydrogen.

9. A compound of claim 1, wherein $R_3$ and $R_4$ together with carbon to which they are bonded form a phenyl ring and $L_1$ and $L_2$ together form —$CH_1$—$CH_2$—.

10. A compound of claim 1, wherein G is selected from:

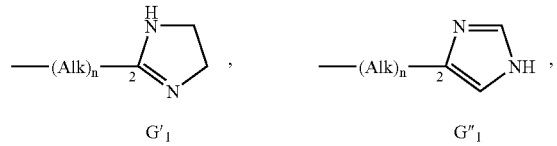

G'$_1$ G''$_1$

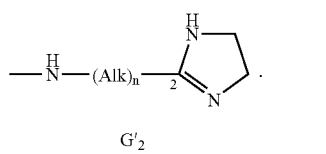

G'$_2$

11. A compound of claim 1, wherein $X_1$ and $X_2$, together with two carbon atoms in the 2 and 3 position of the aromatic ring to which they are bonded, form ($C_4$–$C_7$)cycloalkyl.

12. A compound of claim 1 that is N-[4-chloro-3-(4,5-dihydro-1H-imidazol-2-ylamino) phenyl]-N'-(3-chloro-4-methylphenyl)urea.

13. A compound of claim 1 that is N-(3-chloro-4-methylphenyl)-N'-[2-(1H-imidazol-4-yl)-indan-5-yl]urea.

14. A method for treating a living animal body, including a human, afflicted with a condition selected from depression, anxiety, schizophrenia, Parkinson's disease, cognitive disorders, libido disorders and sexual dysfunction, sleep disorders, drug abuse, and impulsive behaviour disorders, comprising the step of administering to the living animal body, including a human, an amount of a compound of claim 1 which is effective for alleviation of said condition.

15. A pharmaceutical composition useful for treating a living animal body, including a human, afflicted with a condition selected from depression, anxiety, schizophrenia, Parkinson's disease, cognitive disorders, libido disorders and sexual dysfunction, sleep disorders, drug abuse, and impulsive behaviour disorders, comprising as active ingredient a compound of claim 1 in combination with one or more pharmaceutically acceptable, excipients or vehicles.

* * * * *